United States Patent [19]

Rorig et al.

[11] Patent Number: 4,628,095
[45] Date of Patent: Dec. 9, 1986

[54] SUBSTITUTED N-BENZYL-4-(BENZHYDRYL) PIPERIDINES

[75] Inventors: Kurt J. Rorig, Glenview; Stevan W. Djuric, Evanston; Kerry W. Fowler, Chicago; Chi-Dean Liang, Glenview, all of Ill.

[73] Assignee: G. D. Searle & Co., Skokie, Ill.

[21] Appl. No.: 741,648

[22] Filed: Jun. 5, 1985

[51] Int. Cl.[4] ................. C07D 211/10; C07D 211/08
[52] U.S. Cl. ................................. 546/234; 546/235; 546/239
[58] Field of Search ............................... 546/234, 239

[56] References Cited

U.S. PATENT DOCUMENTS 3,014,037 12/1961 Rorig .................................. 546/241
4,035,372 7/1977 Deason et al. .................. 260/293.77
4,356,184 10/1982 Deason et al. ...................... 424/267

FOREIGN PATENT DOCUMENTS 1542823 3/1979 United Kingdom .

OTHER PUBLICATIONS

Abstract of Belgian Pat. No. 862,769, 1/11/77.
J. Y. Lee et al, Meth. and Find. Exptl. Clin. Pharmacol., vol. 5(4) (1983), pp. 235–249.
Lee et al, Chem. Ab. 99: 64024n.

Primary Examiner—Norma S. Milestone
Attorney, Agent, or Firm—Stuart Melton; Steven Odre

[57] ABSTRACT

The invention relates to compounds of the formula:

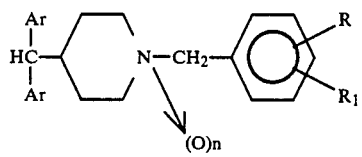

which are useful cardiovascular agents.

7 Claims, No Drawings

SUBSTITUTED N-BENZYL-4-(BENZHYDRYL) PIPERIDINES

BACKGROUND OF THE INVENTION

The present invention provides novel compounds of formula I

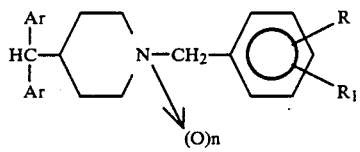

which are pharmacologically useful as cardiovascular agents. More specifically, the compounds of the present invention promote renal, coronary and peripheral vasodilation by the antagonism of calcium ions at arteriolar vessels. Thus, the compounds of the invention are useful generally as vasodilators, and specifically as calcium ion antagonists, antihypertensive agents, and anti-anginal agents, for example.

The present invention also relates to novel pharmaceutical compositions comprising one or more of the active compounds of the invention in combination with suitable pharmaceutical carriers as well as methods of using such compounds and pharmaceutical compositions thereof in the treatment, prevention, or mitigation of cardiovascular diseases or conditions such as arrhythmias, angina-pectoris, hypertension, peripheral vascular disorders, etc. wherein abnormalities in the cellular or vascular handling of calcium ions is a causative factor.

The compounds of formula I comprise (substituted)N-benzyl-4-(benzhydryl)piperidines.

Belgium Pat. No. 862769 discloses diphenyl methylene piperidine derivatives of the formula:

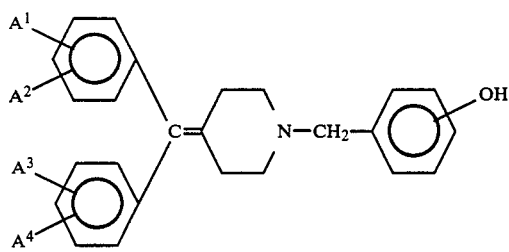

in which $A^1$–$A^4$ are H, halo, halomethyl, alkyl or alkoxy which are indicated to have utility as anti-convulsants and cardiovascular agents. The compounds disclosed in the foregoing Belgium patent are structurally unrelated to the compounds of the present invention by reason of the presence of optionally substituted diphenyl methylene (i.e., C=) attached to the piperidine ring and by the hydroxy substituent on the benzyl moiety which is not present in the compounds of the present invention.

U.S. Pat. No. 4,035,372 discloses 4[[4-(diphenylmethyl)-1-piperidinyl]methyl]benzenamines of the formula

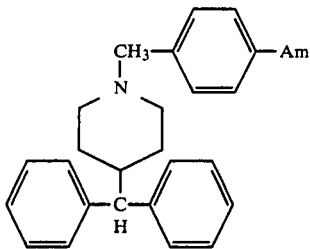

wherein Am represents an amino, alkanoylamino, alkylamino or dialkylamino radical and the vasodilating activity thereof. The compounds of the present invention bear substituents on the benzyl ring in addition to or different than such Am groups.

U.S. Pat. No. 4,356,184 discloses 1-piperidinylmethyl benzenamines of the following formula:

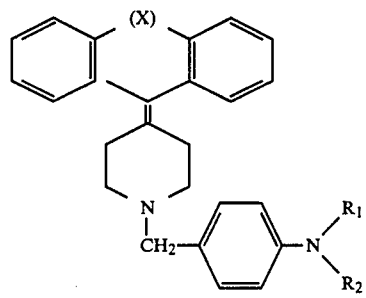

The foregoing compounds represent tricyclic ylidene piperidine derivatives rather than the diarylmethyl compounds of the present invention. Also, the substituents on the N-benzyl group differ in accordance with the practices of the present invention. The compounds disclosed in the aforementioned U.S. Pat. No. 4,356,184 are indicated to be useful as anti-allergic and anti-hypertensive agents.

SUMMARY OF THE INVENTION

The present invention provides compounds of the general formula I:

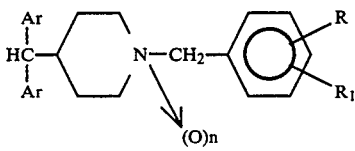

and pharmaceutically acceptable salts thereof wherein Ar are the same or different and represent phenyl or halogen substituted phenyl; R is selected from lower alkoxy or di (lower alkyl) amino; $R_1$ is selected from hydrogen, lower alkoxycarbonyl, carboxy, or lower alkyl aminocarbonyl; and n is 0 or 1 provided that when $R_1$ is hydrogen n is 1.

The compounds and pharmaceutical compositions thereof are useful in the cardiovascular methods of the invention.

DETAILED DESCRIPTION OF THE INVENTION

As used herein, the expressions "lower alkyl" and "lower alkoxy" are defined to include straight or branched carbon-carbon linkages of from about 1 to 6 carbon atoms. Representative alkyl moieties thereof include methyl, ethyl, propyl, butyl, pentyl, sec-butyl, etc. and the corresponding other isomeric forms thereof.

The expression "aryl" includes phenyl or napthyl and substituted derivatives thereof.

The term "halogen" includes bromine, chlorine, and fluorine with chlorine and fluorine being especially preferred.

The compounds herein may also be prepared as addition salt forms thereof and such forms are included in the present compound formulas. Typical of such "pharmaceutically acceptable salts" are those derived from mineral or organic acids including, for example, hydrochloric, hydrobromic, hydroiodic, sulfuric, nitric, acetic, oxalic, maleic, succinic, and the like, as well as hydrated forms thereof.

Exemplary of preferred halo substituted phenyl substituents corresponding to Ar are chloro- or fluoro-phenyl derivatives. Particularly preferred of these are those compounds wherein the halogen is fluoro and both Ar of the benzhydryl moiety are fluoro-phenyl and the fluoro substituent is at the 4-(para) position of the phenyl rings.

With respect to substituents R and $R_1$, especially preferred for R is dimethylamino and for $R_1$ is methoxycarbonyl or t-butyl aminocarbonyl. While $R_1$ may be in the ortho, meta or para position on the phenyl ring and all such position isomers are encompassed herein, particularly preferred compounds are those wherein $R_1$ is in the ortho position.

Representative or preferred compounds in accordance with the present invention are those of the formulae:

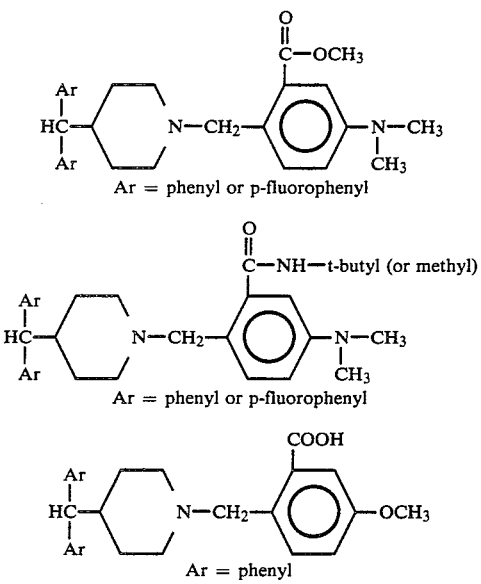

The compounds of the present invention can be administered in such oral dosage forms as tablets, capsules, pills, powders, granules, elixers, or syrups. Likewise, they may also be administered intravascularly, intraperitoneally, subcutaneously, or intramuscularly using forms known to those of ordinary skill in the pharmaceutical arts. In general, the preferred form of administration is oral. An effective but non-toxic amount of the compound is employed in the treatment of hypertension or to promote vasodilation in vascular beds through calcium antagonism, coronary vasodilation, etc. with resultant cardiovascular improvement. The dosage regimen utilizing the compounds of the present invention is selected in accordance with a variety of factors including the type, age, weight, sex, and medical condition of the patient; the severity of the condition to be ameliorated; the route of administration; and the particular compound employed or mixtures thereof. An ordinarily skilled physician can readily determine and prescribe the effective amount of the drug required to prevent, treat or arrest the progress of the condition. Dosages of the compounds of the present invention, when used for the indicated cardiovascular effects (e.g. hypotensive, anti-anginal, coronary dilation or calcium antagonist effect) will range between about 0.2 mg/kg/day to about 0.4 mg/kg/day. The foregoing dosage ranges on a weight basis correspond to a total daily dosage in the average adult patient of between about 15 mg/day to 30 mg/day.

Advantageously, the compounds of the present invention may be administered in a single daily dose. Should it be necessary or desirable, the total daily dosage may be administered in equal divided doses three or four times daily.

In the pharmaceutical composition and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of this invention exhibit antihypertensive activity as determined in the unanesthetized spontaneously hypertensive rat (SHR) assay and/or exhibit calcium ion antagonism as demonstrated in isolated thoracic aorta segments from male spontaneously hypertensive rats. It should be observed that a selected compound may be inactive at a particular test dose in the SHR assay but be active in the calcium antagonist assay and contrariwise. Such compounds may be active at higher doses or by different administration routes or dosing regimens. Moreover, it should be noted that compounds active in the calcium antagonist assay, but inactive in the SHR assay at the same or lower dose, represent advantageous anti-anginal agents, renal or coronary arteriolar dilating agents, etc. consistent with the ultimate cardiovascular utility of the compounds of the present invention.

The test procedures employed to measure the antihypertensive and/or calcium antagonist activity of the compounds of the present invention are described below.

ANTI-HYPERTENSIVE ACTIVITY

Male, unanesthetized spontaneously hypertensive rats, 11 to 16 weeks old were used in this test procedure. The compounds to be tested are administered intragastrically at a dose of 50 mg/kg or intraarterially/intraveneously at a dose of 10 mg/kg. or such other doses determined to be suitable for a specific test compound.

Initial mean arterial blood pressure was measured directly via a previously implanted arterial catheter immediately before administration of the test compound. Blood pressure readings were made at 1, 2, 3, and 4 hours following administration of the test compound. A compound was rated active if the mean post treatment blood pressure of treated rats was significantly different (p less than or equal to 0.05) than that of the control group concurrently administered placebo. Statistical comparisons were made using the paired Student's T test with two sided probability calculations.

The spontaneously hypertensive rat exhibits a genetically-linked hypertension that is similar in most respects to essential hypertension in man. Guanethidine, Apresoline, Aldomet, Clonidine, and Captopril are active in the foregoing hypertensive rat assay and are clinically useful antihypertensive agents.

CALCIUM ANTAGONISM IN VASCULAR SMOOTH MUSCLE

Isolated thoracic aorta segments from the male spontaneously hypertensive rat were utilized in this test procedure.

The excised aorta segment was mounted in a tissue bath containing modified Krebs solution. After depolarization of the tissue with potassium (100 mM), calcium, in cumulative concentrations of $1 \times 10^{-3}M$, $3.2 \times 10^{-3}M$, and $1 \times 10^{-2}M$ was injected into the bath to produce vascular smooth muscle contraction. The developed tension (in grams) is measured and control dose-response values obtained. After one hour of incubation with a test compound at $1 \times 10^{-6}M$ concentration, the same doses of calcium ions were repeated. The log dose-response curves of the control and after treatment were analyzed by linear regression. The $pA_2$ value was calculated as a measure of calcium antagonism of the test compound. See Van Rossum, J. M., Arch. Int. Pharmacodyn, 143, 299-330, 1963. A compound was considered active as a vascular calcium antagonist if the $pA_2$ is 6.0 or greater.

Calcium ions play an essential role in induction and maintenance of vascular smooth muscle contractility. In potassium depolarized vascular smooth muscle, calcium antagonists may block the entry of calcium ions into the cell or act by other mechanisms to inhibit the contractions induced by calcium ions. The inhibition of calcium ion-induced contraction of vascular smooth muscle is used to test compounds for vascular calcium antagonism. Cardiovascular diseases such as arrythmias, angina-pectoris, hypertension, and peripheral vascular disease may be causally related to abnormalities in cellular handling of calcium ions. Calcium antagonists/entry blockers have been proven to be of value in the treatment of the aforementioned cardiovascular diseases or conditions. Verapamil, nifedipine, diltiazem and other drugs are active in the foregoing test and have, likewise, been demonstrated to be clinically useful cardiovascular agents.

The compounds of the present invention are useful antihypertensive agents which advantageously have not been found to produce tachycardia, tachyphylaxis, or orthostatic hypotension and the avoidance or minimalization of such adverse side effects is clearly significant with respect to the ultimate usefulness of the present compounds as cardiovascular agents.

Without being limited to any specific mechanism of action, it is presently believed that the compounds of the invention reduce arterial blood pressure by decreasing total peripheral resistance as a result of arteriolar vasodilation produced by antagonism of calcium ions at the arterioles.

The following non-limiting examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

EXAMPLE 1

Bis(p-fluorophenyl)-4-pyridylmethanol

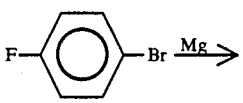

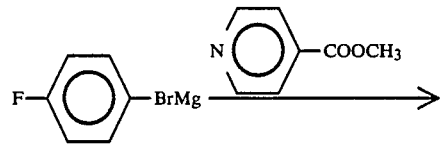

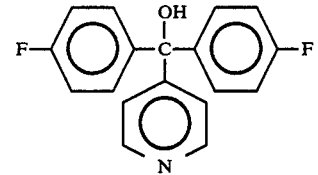

|  | Weight | M.W. | Mmoles |
| --- | --- | --- | --- |
| Bromofluorobenzene | 53.5 g | 175 | 306 |
| Mg metal | 7.3 g | 24.3 | 300 |
| Methyl isonicotinate | 21 g | 137.1 | 153 |

The reaction was run under a $N_2$ atmosphere. The bromofluorobenzene reactant was dissolved in 120 mL of dry ether. 23 mL of this solution was added to a 1 L. dry flask containing 7.3 g Mg shavings and the reaction allowed to proceed. The remaining bromofluorobenzene solution was added and refluxed for an additional hour. Methyl isonicotinate was dissolved in 52 mL of dry ether and added dropwise to the Grignard solution at reflux. The resultant mixture was stirred for 1 hour at room temperature. Saturated $NH_4Cl$ solution was then added until neutral. The resulting light brown solid precipitate was filtered off and allowed to air dry to yield 28.2 g (62%) of the title compound (m.w. 297).

EXAMPLE 2

Bis(p-fluorophenyl)-4-piperidylmethane

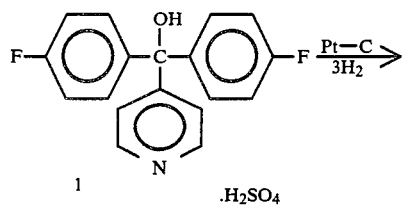
(a)

25.0 g of 1, the sulfate salt of the product of Example 1 [bis-(p-fluorophenyl)-4-pyridylmethanol], was dissolved in 200 mL of a 1:1 mixture of tetrahydrofuran and methanol. 2.5 g of 5% platinum oxide on charcoal catalyst was added and the mixture was hydrogenated on a Parr Shaker hydrogenation apparatus at 60° C. under 60 p.s.i. of hydrogen until three moles of hydrogen had been taken up. The reaction mixture was cooled, the insoluble catalyst filtered and the filtrate was evaporated to dryness to give a quantitative yield of 2.

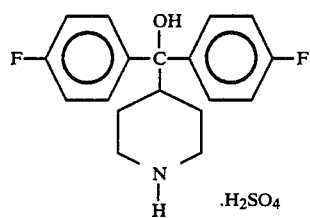
(b)

2 was dissolved in 500 mL toluene and refluxed using a Dean-Stark water trap until the theoretical amount of water had been collected. The solution was then stripped to dryness on a steam bath at 15 mm pressure. A quantitative yield of pale yellow 3 was obtained.

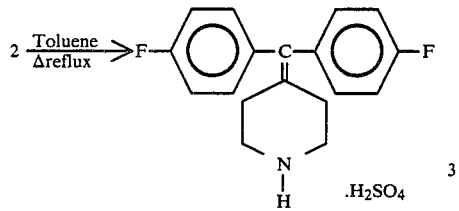
(c)

The residual compound 3 was dissolved in 150 mL methanol, 2.5 g of 10% palladium on charcoal was added and the resulting suspension heated to 60° C. on the Parr-Shaker hydrogenation apparatus until the theoretical one mole of hydrogen had been taken up. The solution was cooled, the catalyst filtered off and the filtrate was heated on the steam bath at 15 mm pressure to strip off all methanol. The residual solid was covered with 200 mL water and 200 mL ether. 1N aqueous NaOH was added with shaking and stirring until all the solid had dissolved. The ether layer was separated, dried over magnesium sulfate and evaporated to dryness. This gave 25 g of bis(p-fluorophenyl)-4-piperidylmethane.

EXAMPLE 3

2-[[4-[bis(4-fluorophenyl)methyl]-1-piperidinyl]methyl]-5-(dimethylamino)-N-(1,1-dimethylethyl)benzamide

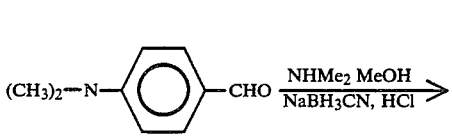

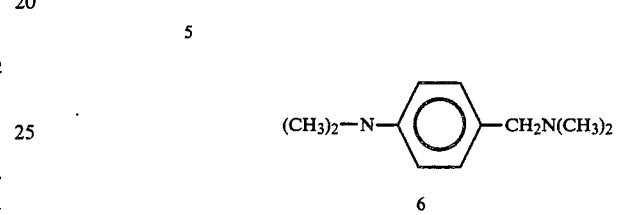

Dimethylamine (27.0 g, 0.6 mole) was dissolved in methyl alcohol (100 mL) and 10N HCl in methanol (0.2 mole) added dropwise. p-Dimethylamino benzaldehyde (14.9 g, 0.1 mole) was added in portions along with several (ca. 20) Linde 3A molecular sieves. The mixture was stirred under N₂ for 20 min and then NaBH₃CN (4.4 g., 0.07 mole) was added in one portion. Stirring was continued at room temperature for 10 hours. The reaction mixture was filtered and evaporated in vacuo. The residue was partitioned between ether (200 mL) and water (50 mL). The ether layer was separated and the aqueous layer extracted with more ether (3×100 mL). Evaporation of the dried ether extracts (Na₂SO₄/K₂CO₃) afforded 20.2 g of crude product which thin layer chromatography (CH₂Cl₂) showed to be comprised of two main spots.

The materials were separated by solubility properties (in ether) and the faster moving spot was purified by distillation. The low R$_f$ material was extremely insoluble in organic solvents and water. The desired dimethylaminomethyl product was a distillable material (b.p. 90° C. at 4 mm Hg). The hydrochloride salt had the following spectra.

Spectral data

NMR (d₆, DMSO, 60 MHz): 2.15 (3H, s, (CH₃)₂N), 3.0 (6H, s (CH₃)₂N), 4.15 (2H, s, —CH₂N+), 6.8 (2H, d, ArH's), 7.3 (2H, d, Ar H's).

Reaction (a) was repeated yielding 20.1 g of desired product purified by bulb to bulb distillation.

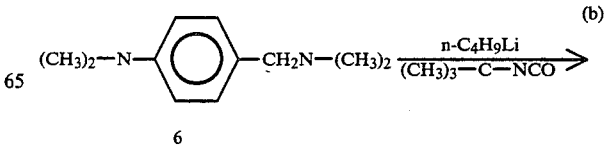
(b)

-continued

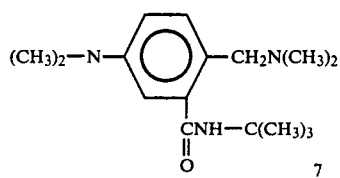
7

Compound 6 (1.99 g, 0.011 mole) was dissolved in anhydrous ether (10 mL) with stirring under N₂.

The solution was stirred at 0° C. and n-butyl lithium (1.6N in hexane, 7.3 mL, 1.05 equivalents) added via a syringe. The mixture was allowed to stir at room temperature overnight. At this point, a small aliquot of the reaction mixture was withdrawn and quenched with D₂O. The balance was stirred at −78° while a solution of t-butyl isocyanate (1.15 g, 0.0115 mole) in ether (20 mL) was added via a syringe. The mixture was slowly allowed to warm to room temperature and poured into cold NH₄Cl solution (10 mL). The aqueous layer was separated and washed 3× with ether (3×25 mL). The combined ethereal extracts plus the original layer were washed with sat. NaCl (15 mL) and dried (MgSO₄). Evaporation of the volatiles in vacuo afforded 2.6 g of crude product. TLC (CH₂Cl₂:MeOH:Et₃N) showed that two major components were evident, one being starting material.

The material was chromatographed on Merck Kieselgel 9.(250 g, CH₂Cl₂:2% MeOH:1% Et₃N).
Eluted were
(a) Combined fractions containing multicomponent mixtures
(b) The desired trisubstituted product, 1.6 g, as a gum.
(c) Starting amine, 0.5 g Yield of desired product was 53% (not taking recovered starting material into account).

Spectral Data:
NMR (60 MHz; CDCl₃) δ: 1.7 (9H, s, N-t-butyl), 2.4 (6H, s, NMe₂), 3.2 (6H, s, NMe₂), 3.6 (6H, s, NMe₂) and 6.8–7.3 (3H, m, ArH's).
IR: 3220, 1660, 1610, 1570, 1310, 1230 cm⁻¹
M.S.: m/e 377 (M+), 343.

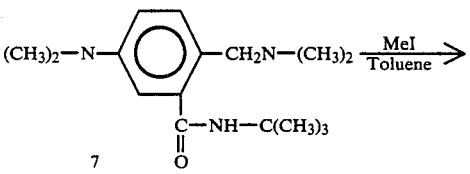
(c)

To a solution of 7 in anhydrous toluene (20 mL) was added methyl iodide (0.32 mL) via a dry syringe. The mixture was stirred under nitrogen at 0° C. for 35 minutes and then allowed to slowly warm to room temperature over a period of 40 minutes. The reaction mixture was then stirred at room temperature for 10 hours, at which point the white precipitate was filtered off on sinter glass. The filtrate was evaporated to dryness and unchanged starting material was recycled. The weight of the first crop of salt was 1.2 g and the weight of starting material recovered was 0.58 g; second crop of recycled material=0.5 g.

Spectral data:
NMR (d₆DMSO) δ: 1.4 (9H, s, t-butyl), 3.05 (15H, s, N—Me₂ and N+Me₃) 4.7 (2H, s, —CH₂N+), 6.8 (2H, ArH's), 7.5 (1H, ArH's) 8.05 (1H, s, —CONH).
IR (KBr) 3510, 3300, 1650, 1600, 1370 cm⁻¹.

(d)

8 —DMF, NaI→

9

A mixture of 8(0.34 g, 0.0012 mole) and 4 (0.5 g, 0.0012 mole) was dissolved in anhydrous DMF (5 mL) containing NaI (5 mg). The mixture was heated at 70° C. for 24 hr. and then the majority of the solvent was removed. The residue was partitioned between water (5 mL) and methylene chloride (20 mL). The methylene chloride fraction was separated, washed with H₂O (2×10 mL) and brine (10 mL). Evaporation of the dried (Na₂SO₄) solvent in vacuo afforded a light orange gum which was purified by column chromatography to yield the title product.

Spectral data:
NMR: ('H, δ, CDCl₃, 60 MHz) 0.00–2.2 (piperidyl Hs), 1.4 (9H, s, t-butyl), 2.9 (6H, s, NMe2), 3.4(2H, s, CH₂—N), 3.45 (piperidyl Hs), 6.5–7.3 (11H, 8, ArHs), 9.2(1H, brs, N—H)
IR: (CHCl₃): 3220, 1650, 1610, 1510 cm⁻¹

EXAMPLE 4 methyl 2-[[4-[bis(4-fluorophenyl)methyl]-1-piperidinyl]methyl]-5-(dimethylamino)benzoate (a)

6 —n-C₄H₉Li/CO₂→ (CH₃)₂—N—⬡—CH₂N—(CH₃)₂
                                    |
                                    CO₂Li

10

6 was lithiated as described in Example 3 (24 h, room temperature). The reaction mixture was cooled to −28° C. (CCl₄/CO₂) and the solution of the lithio salt added via syringe to a saturated solution of CO₂ in ether. An immediate precipitation occurred upon the addition. After the addition was complete the solid precipitate was filtered (sintered glass) and dried in vacuo (40° C.) overnight to afford the lithio carboxylate (2.4 g).

This material was used directly for the next reaction.

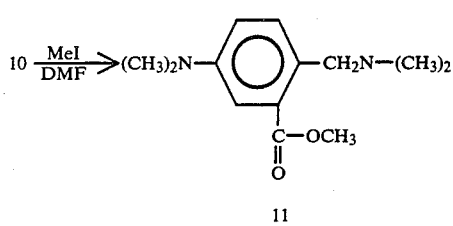
(b)

10 (2.1 g, 0.0092 mole) was dissolved in anhydrous DMF (30 mL) and methyl iodide (1.3 g, 0.57 mL) added via a syringe. Stirring was continued at room temperature under N₂ for 7 hours. The mixture was then partitioned between Et₂O (80 mL) and water (20 mL). The ether layer was separated and the aqueous layer washed 3× with ether (3×40 mL). The combined ether extracts were washed with brine (2×30 mL), dried (Na₂SO₄) and evaporated in vacuo to afford 1.8 g of crude product. TLC (CH₂Cl₂:7% MeOH) revealed two spots. The mixture was applied to a silica gel column and purified by the flash technique of Still (W. C. Still, M. Kahn, A. Mitra, *J. Org. Chem.*, 1978, 43, 2923–2925) eluting with CH₂Cl₂ and then CH₂Cl₂:5% MeOH. Thus obtained was 1.6 g of pure product (62% yield)

Spectral data:

NMR (CDCl₃)δ: 3.0 (6H, s, NMe₂), 3.35 (6H, s, NMe₂), 3.9 (3H, s, —OCH₃), 5.2 (2H, s, CH₂N), 6.85 (1H, dd ArH), 7.35 (1H, d, ArH), 7.7 (1H, d, ArH).

IR(CHCl₃):2980, 1720, 1610, 1270, 870 cm⁻¹.

U.V. (MeOH), 222, 282 nm.

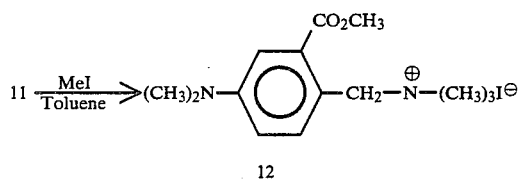
(c)

The procedure of Example 3(c) was followed with stirring under N₂ for 10 hours. The precipitated quaternary salt was filtered on sintered glass and weighed (0.54 g). The recovered starting material was recycled and treated with a further equivalent of methyl iodide. After prolonged stirring and standing, a further 1.0 g of material was isolated.

Spectral data:

NMR (CD₃OD)δ: 3.0 (15H, s, Me₃N⁺, NMe₂), 3.85 (3H, s, OCH₃), 4.85 (2H, s, CH₂—N), 6.9 (1H, d, d, ArH), 7.4 (2H, m, ArH's).

IR (KBr):3480, 1705, 1605, 1220 cm⁻¹.

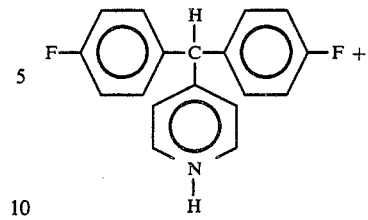
(d)

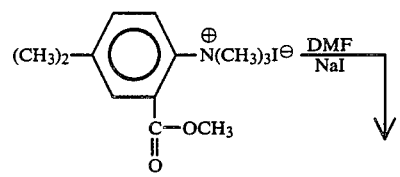

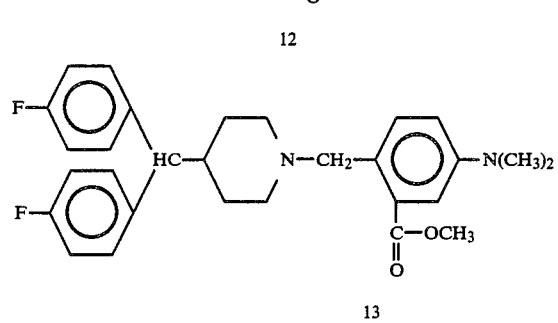

A mixture of 12 (0.4 g, 0.0011 mole) and 4 (0.31 g) was dissolved in anhydrous DMF (2 mL) containing NaI (5 mg). The mixture was heated at 70° C. for 24 hours and then the majority of the solvent was removed under high vacuum. The orange residue was partitioned between water (5 mL) and methylene chloride (20 mL). The organic layer was separated and the aqueous layer washed with more methylene chloride (2×20 mL). The combined organic extracts were washed with water (1×10 mL) and brine (1×10 mL). Evaporation of the dried (Na₂SO₄) solvent in vacuo afforded 0.5 g of a light orange gum which was purified by column chromatography (Merck Kieselgel 9, CH₂Cl₂:5% MeOH as eluant). 410 mg of the desired product 13 was isolated.

Spectral data

NMR (¹H,CDCl₃,60 MHz) δ: 1.2–4.5 (10H, m, Piperidyl H's+ArC—H), 2.9 (6H, s, N-(CH₃)₂), 3.7 (2H, s, —CH₂N—) 3.85 (3H, s, OCH₃) 6.6.7.5 (11H, m, Ar Hs)

IR (CHCl₃): 1718, 1660, 1600, 1500, 1230 cm⁻¹.

EXAMPLE 5

5-(dimethylamino)-2-[[4-(diphenylmethyl)-1-piperidinyl]methyl]-N-methylbenzamide

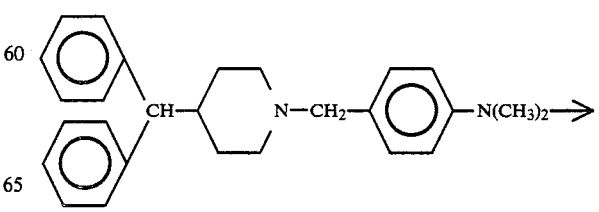

-continued

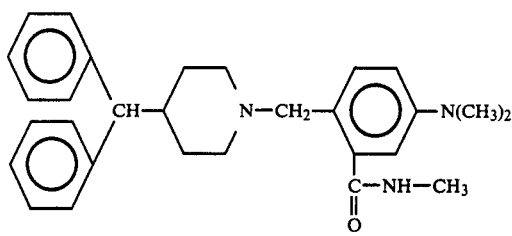

15

The reaction was carried out under N₂ atmosphere. All glassware was previously dried.

Compound 14 (5 g, 13 mmole), prepared according to Example 4B, U.S. Pat. No. 4,035,372, was dissolved in 50 mL of ether and the solution cooled to 0° C. 7.7 ml of 1.95M n-butyl lithium in hexane was added and the resulting mixture stirred at room temperature for 4 days. The solution was cooled to −78° C. and 798 mg of methyl isocyanate dissolved in 5 ml (14 mmole) of ether added and the solution allowed to gradually come to room temperature and stirred for 6 hr. Saturated NH₄Cl solution was added until neutral. Following extraction with ether and drying over MgSO₄, column separation yielded 2 g of 15 as a white solid (35% yield)

Spectral data:

NMR ($^1$H, CDCl₃, 60 MHz) δ: 1.2–4.5 (10H, piperidyl H's and Ar C—H), 2.9–3.0 (9H, NMe), 3.4 (2H, m, CH₂Ar), 6.9–7.5 (13H, m, Ar H's).

IR (KBr): 3450, 3330, 1660, 1600 cm$^{-1}$.

EXAMPLE 6

5-(dimethylamino)-N-(1,1-dimethylethyl)-2-[[4-(diphenylmethyl)-1-piperidinyl]methyl]benzamide

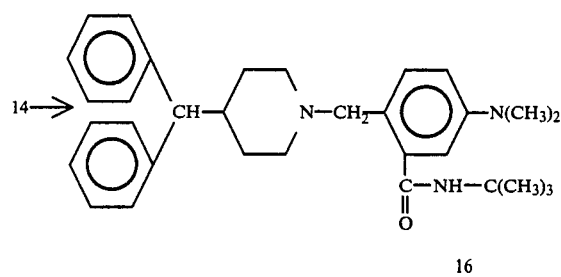

16

The procedure of Example 5 was repeated using 1.4 g of t-butyl isocyanate in place of methyl isocyanate. 2.07 g of 16 was recovered as a white solid.

EXAMPLE 7

2-[[4-(diphenylmethyl)-1-piperidinyl]methyl]-5-methoxybenzoic acid

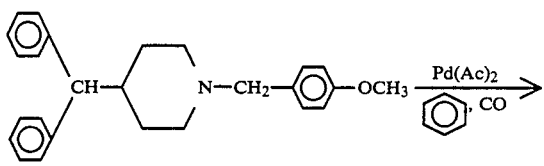

17

-continued

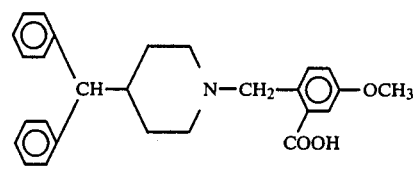

18

Compound 17 was first prepared as follows:

4-(Diphenylmethyl)-piperidine (25.5 g, 0.1 mole; Reilly Tar and Chemical Co.) and p-methoxybenzylchloride (17.0 g, 0.109 mole) [prepared according to Rorig et al. Organic Synthesis, Collective Vol. IV, p. 576] were dissolved in 200 mL butanone. 10.0 g of powdered anhydrous potassium carbonate (150 mesh) was added. The reaction was stirred vigorously while heating to reflux for 24 hours. The solids were removed by filtration and the filtrate was evaporated to dryness at reduced atmosphere pressure (20 mm of mercury) to yield 17 which was used in subsequent reactions. The residual solid was dissolved in 300 mL anhydrous ether and dry HCl gas was bubbled in to precipitate the hydrochloride salt of N-(p-methoxybenzyl)-4-(diphenylmethyl) piperidine. This was recrystallized from 200 mL hot ethanol to which one liter of anhydrous ether was added to give 30.2 g of product as the hydrochloride salt. (81% yield, m.p. 284°–286°).

(Calc'd) C: 76.54: (Found) 76.21; (Calc'd) H: 7.41: (Found) 7.81; (Calc'd) Cl: 8.69: (Found) 8.77.

3.6 g (10 mmole) of 17 and Pd (OAc)₂ (1.98 g, 12 mmole) in 100 mL of benzene were stirred under argon for 4 days and then shaken with CO at 35 psi and maintained at a CO pressure above 10 psi for 3 hr. 3 mL of water was added and the mixture was filtered. Following removal of solvent from the filtrate, purification by column chromatography and recrystallization from AtOAc, the desired product 18 was obtained (mp 246°–250° C.)

Spectral data:

NMR (CDCl₃) δ: 3.5 (d, J=10 Hz, 1H), 3.75 (2H, s), 3.85 (3H, s).

IR (CHCl₃): 3450, 1640, 1610 cm$^{-1}$.

EXAMPLE 8 methyl 2-[[4-(diphenylmethyl)-1-piperidinyl]methyl]-5-methoxybenzoate

The methyl ester of the carboxylic acid 18 of Example 7 was obtained using the same procedure except 10 ml of MeOH was added to the initial reaction mixture:

Spectral data:

NMR (CDCl₃) δ: 3.42 (2H, s), 3.5 (d, J=10H₂, 1H) 3.77 (3H, s), 3.82 (3H, s).

IR (CHCl₃): 1720 cm$^{-1}$.

EXAMPLE 9

4-[[4-(diphenylmethyl)-1-piperidinyl]methyl-N,N-dimethylbenzeneamine, $N^4$-oxide

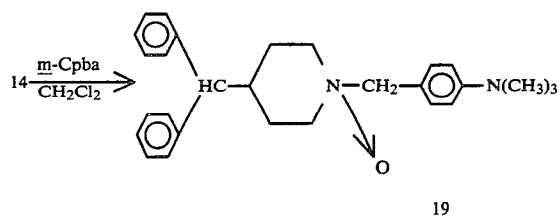

19

Compound 14 was prepared according to the procedure of Example 4B of U.S. Pat. No. 4,035,372. 1.5 g of 14 (0.004 mole) was dissolved in distilled dichloromethane (25 mL)($N_2$, magnetic stirring, 0° C.) and m-CPBA (0.7 g, 0.004 mole) added in portions over a period of 5 minutes. The mixture was allowed to warm to room temperature with m-CPBA being added as necessary. The reaction mixture was evaporated in vacuo and the crude product purified by chromatography (yield—1.1 g)

Spectral data:

NMR ($^1$H, $CDCl_3$) δ: 1.1–3.75 (9H, piperidyl H's, 1H, ArCH), 3.0 (6H, s, $NMe_2$), 4.5 (2H, s, $CH_2NO$), 7.0 (2H, d, ArH's), 7.5–7.8 (12H, ArH's).

IR ($CHCl_3$): 1612, 1525, 1360 $cm^{-1}$.

EXAMPLE 10

5-(dimethylamino)-2-[[4-(diphenylmethyl)-1-piperidinyl]methyl]benzoic acid

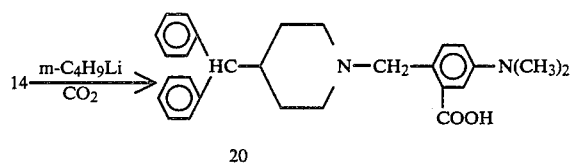

20

A solution of 14 (9.18 g, 23.9 mmole) prepared as before in 100 mL of dry ether under an inert atmosphere was cooled in a dry ice-acetone bath and n-butyllithium (2.14M in hexane, 15.0 mL, 32.1 mmole) was added rapidly by syringe. The reaction mixture was allowed to warm to ambient temperature and stirred for two days. The mixture was recooled in dry ice-acetone and the solution was cannulated into a second flask at dry ice-acetone temperature containing 100 mL ether into which carbon dioxide gas was bubbled continuously. The mixture was allowed to warm to ambient temperature and after stirring overnight the resulting precipitate was filtered off, giving 10.17 g white powder. The filtrate returned 3.50 g of starting material. The product was suspended in water and dissolved by acidifying with an excess of concentrated HCl. The solution was neutralized with aqueous sodium bicarbonate and the resulting precipitate was filtered off, washed with water and dried at 50° C. in vacuo. The hygroscopic white powder (7.49 g, 69%) appeared as a blue fluorescent spot on TLC ($R_f$ 0.15, Merck silica gel 60, 92.5:7:0.5 $CHCl_3$:EtOH:$NH_4OH$). The starting material displays an $R_f$ of 0.48.

Spectral data:

UV max (MeOH): 220 nm (26 500), 272 (18 600);

IR (KBr): 3420 (br), 2950, 1700 (w), 1610, 1560, 1510, 1495, 1450 $cm^{-1}$.

M.S. (m/e): 428(M+,2%), 412 (3), 251 (37), 178 (51), 177 (71), 167 (85), 148 (33), 84 (100).

NMR ($CD_3OD$), δ: 2.95 (6, $NMe_2$), 3.5 (d, $Ar_2CH$), 4.05 (s, 2, $NCH_2$), 6.7 (dd), 7.25 (m, aromatic).

EXAMPLE 11 methyl 5-(dimethylamino)-2-[[4-(diphenylmethyl)-1-piperidinyl]methyl]benzoate

The methyl ester of 20 was prepared as follows.

The free acid 20 (5.10 g, 11.2 mmole) was suspended in 100 mL of ether and acidified with 11.2 mmole of HCl in dioxane. An excess of ethereal diazomethane was added along with enough methylene chloride to effect solution and the reaction mixture was allowed to stir overnight. Removal of the solvents in vacuo gave a residue which was partitioned between methylene chloride and cold aqueous 1N NaOH. Purification of the resulting solid by chromatography on silica gel 60 (gradient 96.75:3:0.25 $CH_2Cl_2$:EtOH:$NH_4OH$) provided 3.19 g of a gummy solid. Salt formation with HCl(gas) in ether/dioxane afforded 3.75 g white powder which contained 1.5HCl and 2$H_2O$ after drying at 70° C. in vacuo. Neutralization with aqueous sodium bicarbonate and ether extraction gave the ester free base as a hygroscopic solid (2.73 g) which analyzed for increasing amounts of water over time even with repeated drying. (Yield ca. 45%.)

Spectral data:

IR ($CHCl_3$): 1720 $cm^{-1}$.

NMR ($CDCl_3$) δ: 7.5–6.5 (m, aryl), 3.81 (s, $CO_2CH_3$, 3H), 2.90 (2, 6H, $NMe_2$), 3.56 (s, N—$CH_2$), 3.46 (d, $Ar_2CH$).

Certain of the preferred compounds of formula I were evaluated for activity in accordance with the test procedures described previously and the results are summarized in Table I.

TABLE I

| Compound Example No. | SHR —mm Hg (dose) | pA2 (Ca++ antagonism) |
| --- | --- | --- |
| 3 | −54 (50 mpk-oral) | inactive |
| 4 | −67 (50 mpk-oral) | 7.78 |
| 5 | −56 (10 mpk-i.v.) | 7.25 |
| 6 | inactive | 7.20 |
| 8 | −40 (3–10 mpk-i.v.) | —* |
| 9 | −48 (50 mpk-oral) | inactive |
| 11 | −34 (50 mpk-oral) | 7.65 |

*not tested

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations

What is claimed is:

1. A compound of the formula

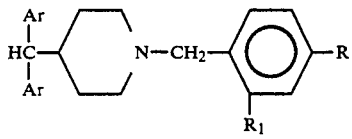

and the pharmaceutically acceptable salts thereof wherein Ar are the same or different and represent phenyl or halogen substituted phenyl; R is di (lower alkyl) amino; and $R_1$ is carboxy, lower alkoxy-carbonyl or lower alkylaminocarbonyl.

2. A compound according to claim 1 which is methyl 5-(dimethylamino)-2-[[4-(diphenylmethyl)-1-piperidinyl]methyl]benzoate.

3. A compound according to claim 1 which is 5-(dimethylamino)-2-[[4-diphenylmethyl)-1-piperidinyl]-methyl]benzoic acid.

4. A compound according to claim 1 which is 5-(dimethylamino)-N-(1,1-dimethylethyl)-2-[[4-(diphenylmethyl)-1-piperidinyl]methyl]benzamide.

5. A compound according to claim 1 which is 2-[[4-[bis(4-fluorophenyl)methyl]-1-piperidinyl]methyl]-5-(dimethylamino)-N-(1,1-dimethylethyl)benzamide.

6. A compound according to claim 1 which is methyl 2-[[4-[bis(4-fluorophenyl)methyl]-1-piperidinyl]methyl]-5-(dimethylamino)benzoate.

7. A compound according to claim 1 which is 5(dimethylamino)-2-[[4-(diphenylmethyl)-1-piperidinyl]methyl]-N-methylbenzamide.

* * * * *